(12) United States Patent
Edens

(10) Patent No.: US 6,316,937 B1
(45) Date of Patent: Nov. 13, 2001

(54) METHOD AND APPARATUS FOR DETECTING AND MEASURING AXIALLY EXTENDING DEFECTS IN FERROUS TUBE

(75) Inventor: Brian Wade Edens, San Antonio, TX (US)

(73) Assignee: Oilfield Equipment Marketing, Inc., San Antonio, TX (US)

(*) Notice: Subject to any disclaimer, the term of this patent is extended or adjusted under 35 U.S.C. 154(b) by 0 days.

(21) Appl. No.: 09/417,554

(22) Filed: Oct. 13, 1999

(51) Int. Cl.[7] .................................................. G01N 27/72
(52) U.S. Cl. .......................... 324/220; 324/235; 324/229; 324/242; 702/38
(58) Field of Search ...................... 324/220, 232, 324/229, 227, 221, 235, 240, 242; 702/85, 86, 189, 38, 33–36, 59, 57, 113; 73/151

(56) References Cited

U.S. PATENT DOCUMENTS

| | | | |
|---|---|---|---|
| 4,492,115 | 1/1985 | Kahil et al. | 73/151 |
| 4,555,665 | 11/1985 | Stanley et al. | 324/229 |
| 4,611,170 | 9/1986 | Stanley et al. | 324/229 |
| 4,636,727 | 1/1987 | Kahil et al. | 324/227 |
| 4,710,712 | 12/1987 | Bradfield et al. | 324/227 |
| 4,792,756 | 12/1988 | Lam et al. | 324/232 |
| 5,671,155 | 9/1997 | Edens et al. | 364/507 |
| 5,943,632 | 8/1999 | Edens et al. | 702/38 |

*Primary Examiner*—Safet Metjahic
*Assistant Examiner*—Anthony Jolly
(74) *Attorney, Agent, or Firm*—Christopher L. Makay

(57) ABSTRACT

An apparatus for detecting and measuring axially extending defects in ferrous tube includes a magnetizing coil for inducing a longitudinal magnetic field in the ferrous tube. Linear magnetic transducers are used to detect parallel non-linking flux leakage that occurs from axially extending defects. An analog to digital converter digitizes the measured signals representing the amount of parallel non-linking flux leakage detected. A processor subtracts signals typical of ferrous tube with no axially extending defects from the measured signals. The processor further processes the resulting signals after subtraction, by separating the alternating AC components from the constant DC components to remove the effects of perpendicular flux leakage, which may exist in the measured signals. The processor then calculates the percentage of missing material due to the axially extending defects by applying a proportionality equation to the remaining DC components of the measured signals. A screen and/or printer displays to the end user the percentage of missing material detected.

26 Claims, 10 Drawing Sheets

METHOD AND APPARATUS FOR DETECTING AND MEASURING AXIALLY EXTENDING DEFECTS IN FERROUS TUBE

BACKGROUND OF THE INVENTION

1. Field of the Invention

The present invention relates to the detection of defects in ferrous tubes and, more particularly, but not the way of limitation, to a method and apparatus that employs small area magnetic transducers to sense non-linking parallel flux leakage coupled with digital signal processing to discretely locate and accurately measure axially oriented thickness deviations in the homogeneous body wall of ferrous oil field tubular products.

2. Description of the Related Art

Several types of ferrous tubular products are used in a typical oil field production well system. A production well system can require tubular casing, production tubing, continuous length coiled tubing, sucker rod and a drill string. These ferrous oil field tubular products must be inspected after manufacturing and periodically during use to determine if defects or flaws exist within the homogeneous material.

A variety of defects can exist in ferrous oil field tubular products and have been previously located or detected using several techniques and methods. Localized, discrete defects such as pits, cracks, pin holes and other small, localized defects are detected by inducing a longitudinally oriented constant DC magnetic field into a ferrous tubular product while monitoring for perpendicular magnetic flux leakage with some form of magnetic sensing device, oriented parallel to the surface of the ferrous tube, such as a Hall Effect sensor, induction coil or magneto-resistor. One such system is described in U.S. Pat. No. 5,671,155, which issued Sep. 23, 1997 to EDENS. However, longer, larger, axially extending defects which are typically greater than one inch in length, such as sucker rod wear, erosion/corrosion and co-rod wear, have typically been harder to detect or totally undetectable with perpendicular magnetic flux leakage prior art methods. Often, these types of defects occur at such a gradual rate that little or no perpendicular magnetic flux leakage is generated for detection.

Axially extending defects have been detected with prior art such as the magnetic rotating pole method, the rotating gamma radiation instrument, the electrically rotated magnetic eddy current technique and the saturated magnetic field induction method. Although prior art methods have provided some means of detecting axially extending defects in ferrous oil field tubular products, they suffer from several disadvantages including the requirement of movement, insensitivity to less severe defects, less than one hundred percent coverage of the ferrous tube under inspection, unreasonable cost and size, inaccuracies that yield erroneous results and safety hazard issues.

U.S. Pat. No. 4,555,665, issued Nov. 26, 1985, and U.S. Pat. No. 4,611,170, issued Sep. 9, 1986, both to STANLEY, disclose an apparatus to measure the average wall thickness of ferrous tubing. This is accomplished by integrating an induced voltage in an induction pickup coil, which is induced by changes in the total saturating magnetic field applied to the ferrous tubing by a DC magnetic field generating coil. However, the average wall thickness apparatus does not utilize magnetic flux leakage to obtain the average wall thickness, as stated within the above mentioned patents. This fact would be obvious to one skilled in the art because magnetic flux leakage is not readily detectable away from the surface of a ferrous tubing product since flux leakage decays at an exponential rate through air. This technique also requires movement of the apparatus to induce a sufficiently large voltage change on the induction pickup coil to be measurable, and therefore the reason why integration is used to create a sum of the detected voltages over time. Moreover, an average wall thickness measurement is much less desirable than a discrete, pinpoint measurement.

Prior art gamma radiation systems fail to detect axially extending defects because of the typical eighteen inch helix which is generated from the rotation of the radioactive source around the circumference of the ferrous tubular product as the tubular product is passed through the detection system. A sucker rod wear that is less than eighteen inches in length can easily be missed as the radioactive tool spins around the problem area. Also, since the radioactive beam typically passes through both walls of the ferrous tube to reach the photo-multiplier, which turns the detected radiation into electrical voltage, the result is actually an average thickness of the two points of measurement on the ferrous tube walls. Another detractor of this method is the radioactive source. Much cost and precaution must be taken when handling and operating these older inspection systems, only to yield inadequate results.

The rotating pole magnetic method used in prior art has seen limited use in the past decade due to the immense size and cost of the apparatus required to magnetize typical ferrous oil field tubular products. A typical apparatus to sufficiently magnetize a ferrous tube can weigh in excess of 3000 pounds and is extremely costly to manufacture, therefore making it largely undesirable to implement. Also, this technique requires that the magnetic field be transferred from one pole of the magnet, through the air, into the ferrous tube under inspection, back through the air and into the opposite pole of the magnet as the device spins around the ferrous tube. The spinning of the poles creates a circular, transverse field which, in turn, generates perpendicular flux leakage from longitudinally oriented defects. The ferrous tube acts as a core and means of transmission for the magnetic field. Those of ordinary skill in the art know that magnetic fields decay exponentially through air and is the reason why this magnetizing device must be so large. It is necessary to generate as much as 20,000 gauss to properly saturate a ferrous tubular product with this technique.

U.S. Pat. No. 4,492,115, issued Jan. 8, 1985, and U.S. Pat. No. 4,636,727, issued Jan. 13, 1987, both to KAHIL; U.S. Pat. No. 4,710,712, issued Dec. 1, 1987 to BRADFIELD; and U.S. Pat. No. 4,792,756, issued Dec. 20, 1988 to LAM all disclose an apparatus that detects axially extending defects in ferrous oil field tubing products using an electrically rotated magnetic eddy current method. These apparatuses induce a magnetic AC eddy current around the circumference of the ferrous tubing, which requires a separate set of wire windings to be placed around the circumference of the tube in addition to the windings that are used to induce a constant DC magnetic field into the tubing. These extra windings must be wound with a sine and cosine configuration, to detect thickness variations. Although the apparatuses do not spin, the magnetic AC eddy current field is rotated electrically. One set of sender windings generates a magnetic AC eddy current field in the ferrous tube while a second set of receiver windings provides an AC voltage by the induction method as the AC eddy current propagates through the ferrous tube body wall. The sender and receiver windings are situated as pairs in four quadrants around the circumference of the ferrous tubing, are activated in pairs, and are ninety degrees apart from one another. The measured AC voltage from the receiver winding is monitored for phase and amplitude change and compared to values that have been determined through laboratory testing to extrapolate into the amount of missing material in the body wall of the ferrous tube in the ninety-degree span. However, this technique yields erroneous results if more than one defect exists within the ninety degree span, which is very common in ferrous oil field tubular products. Having multiple defects in the ninety-degree span changes the phase and amplitude of the magnetic AC eddy current more than one time, which yields incorrect results because the phase and amplitude change is no longer relative to the laboratory tested values. Also, these apparatuses require both a constant DC magnetic field and a magnetic AC eddy current field, which must be electrically rotated, to obtain results. The DC magnetic field is used to help obtain better saturation into the ferrous tube body wall because AC eddy currents decay through both air and ferrous material at an exponential rate, similar to ultrasonic waves.

Accordingly, a method and apparatus that can detect axially extending defects in ferrous oil field tubular products, but does not have the requirement of movement; does not require an extremely large, expensive apparatus to rotate a DC magnetic field; and does not require an additional magnetic AC eddy current field would be a vast improvement over the aforementioned systems. Also, an apparatus that provides one hundred percent coverage of the ferrous tubing with the ability to accurately measure multiple defects within the same cross sectional portion of the tubing without erroneous results which utilizes a testing method that poses no hazardous working conditions would be a great improvement in the art of ferrous tubular inspection.

SUMMARY OF THE INVENTION

In accordance with the present invention, a ferrous tube tester detects axially extending defects in the homogeneous body wall of the tube. The ferrous tube tester uses digital signal processing techniques to separate voltages generated by perpendicular flux leakage from voltages generated by parallel non-linking flux leakage to measure axially extending thickness deviations within the ferrous tube body wall.

A constant DC saturating longitudinal magnetic field is induced into the ferrous tube. The ferrous tube tester and the ferrous tube are moved in relation to one another to cover the full length of the ferrous tube. However, it should be understood that the ferrous tube tester does not require movement to obtain a measurement of ferrous tubing wall thickness. This allows for static mode operation and, in some applications, can allow for an automated inspection apparatus to pin point the exact location of a defect within the ferrous tubing.

An array of small area magnetic transducers, such as linear Hall effect sensors, contained within a protective housing, are positioned edge to edge around the circumference of and in contact with the outer surface of the ferrous tube. The magnetic transducers are oriented perpendicular to the surface of the ferrous tube as required for sensing the desired magnetic fields. It is necessary to use a magnetic transducer so the ferrous tube tester has the ability to operate without movement.

The voltages generated by the magnetic sensors are fed into a processor or digital computer of the ferrous tube tester for digitizing, comparison to pre-determined values, and digital signal processing, which isolates DC voltages generated from the parallel, non-linking flux leakage. The processor or digital computer then calculates the percentage of missing material due to the axially extending defects by applying a proportionality equation to the remaining DC components of the measured signals. A screen and/or printer display to the end user the percentage of missing material detected.

It is, therefore, an object of the present invention to provide a ferrous tube tester that employs magnetic transducers to detect the axially oriented wall thickness defects in a piece of ferrous tube.

It is a further object of the present invention to measure the depth of the detected axially oriented wall thickness defects using digital signal processing techniques and the application of a proportionality equation.

Still other objects, features, and advantages of the present invention will become evident to those of ordinary skill in the art in light of the following.

DETAILED DESCRIPTION OF THE PREFERRED EMBODIMENT

Figure 1:
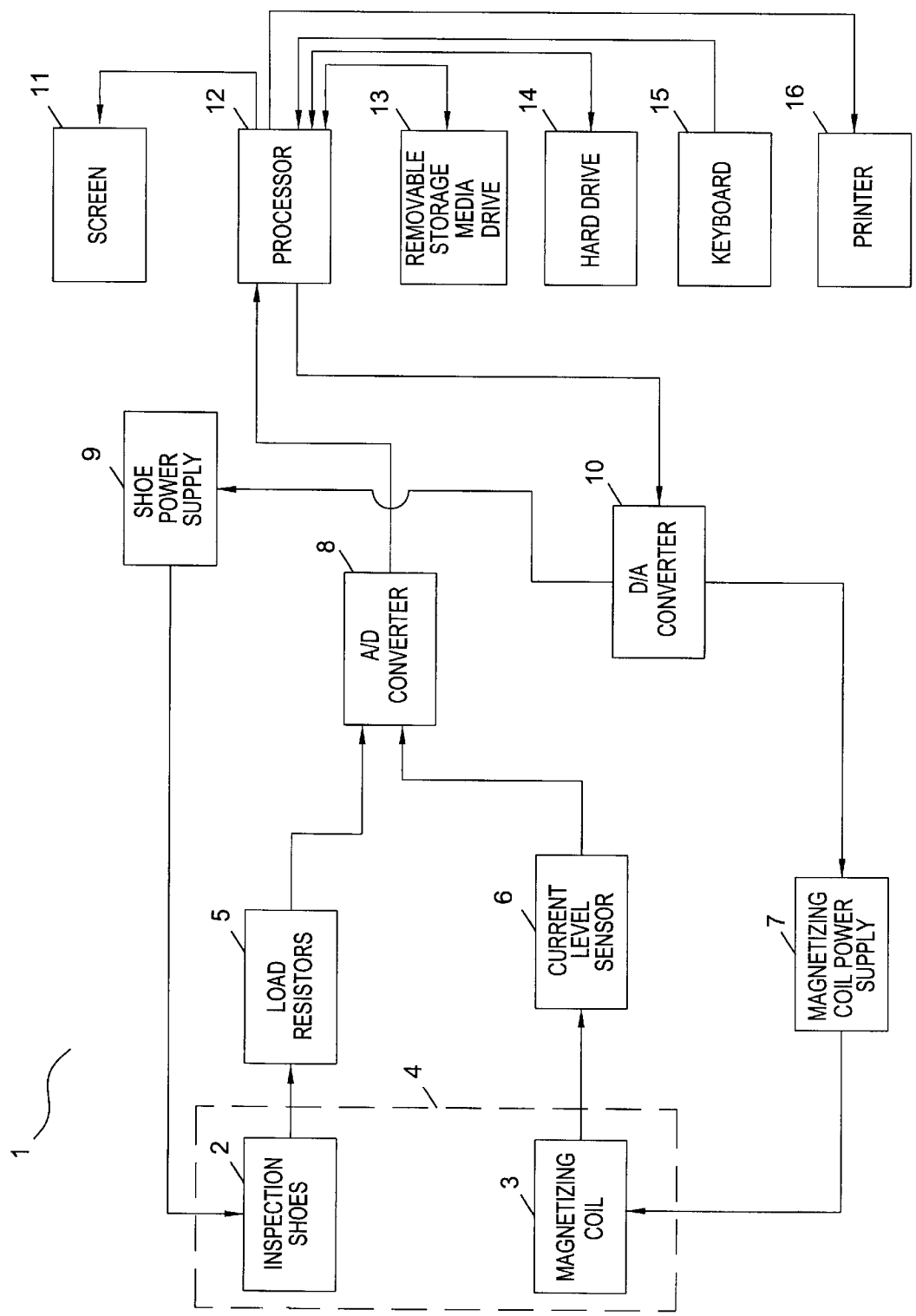
FIG. 1 is a block diagram illustrating the hardware configuration of a ferrous tube tester.

Referring to FIG. 1, ferrous tube tester 1 includes an inspection tool that may be any device capable of inducing a magnetic field in a ferrous tube and then measuring changes in that magnetic field. Such an inspection tool is manufactured by Oilfield Equipment Marketing, Inc., which has a place of business at 4711 Dodge Street, San Antonio, Tex. 78217.

In this preferred embodiment, the ferrous tubing being tested is moved with respect to the ferrous tube tester 1.

However, it should be understood that ferrous tube tester 1 may be moved with respect to the ferrous tubing.

Ferrous tube tester 1 includes inspection head 4 comprised of inspection shoes 2, in which are groups of small area linear Hall magnetic transducers, and magnetizing coil 3. Although this preferred embodiment contemplates the use of linear Hall magnetic transducers, one of ordinary skill in the art will realize that other types of linear magnetic field sensors may be used. Load resistors 5 are included to provide the necessary electrical loading on the linear magnetic transducers for proper operation. Current level sensor 6 provides an accurate measurement of the amount of DC current flowing through magnetizing coil 3 so that processor 12 may keep the current level stable. Magnetizing coil power supply 7 is a voltage controlled power supply that provides sufficient current for magnetizing coil 3 to completely saturate a tested ferrous tube with a DC magnetic field. A/D converter 8 provides for processor 12 a digital representation of the analog voltages output from inspection shoes 2 and current level sensor 6. Shoe power supply 9 provides a constant voltage to inspection shoes 2. Processor 12 turns shoe power supply 9 on and off as needed through an on-board relay. D/A converter 10 provides analog voltages equivalent to digital signals sent by processor 12 to control shoe power supply 9 and magnetizing coil power supply 7. D/A converter 10 contains many digital to analog conversion channels to allow processor 12 to control many items simultaneously. Screen 11 displays to the end user all system functions and wall thickness results calculated by processor 12. Processor 12 monitors the linear Hall transducers in inspection shoes 2 through A/D converter 8. Processor 12 also performs all necessary digital signal processing required to obtain axially extending defect depth measurements from the tested ferrous tube. Removable storage media drive 13 is provided to archive all data collected during the testing process for later retrieval. Hard drive 14 provides the operating software to processor 12. Keyboard 15 provides a means for the end user to interact with processor 12, as input is required. Printer 16 can print charts that show the results from a test run performed on a ferrous tube.

Figure 2:
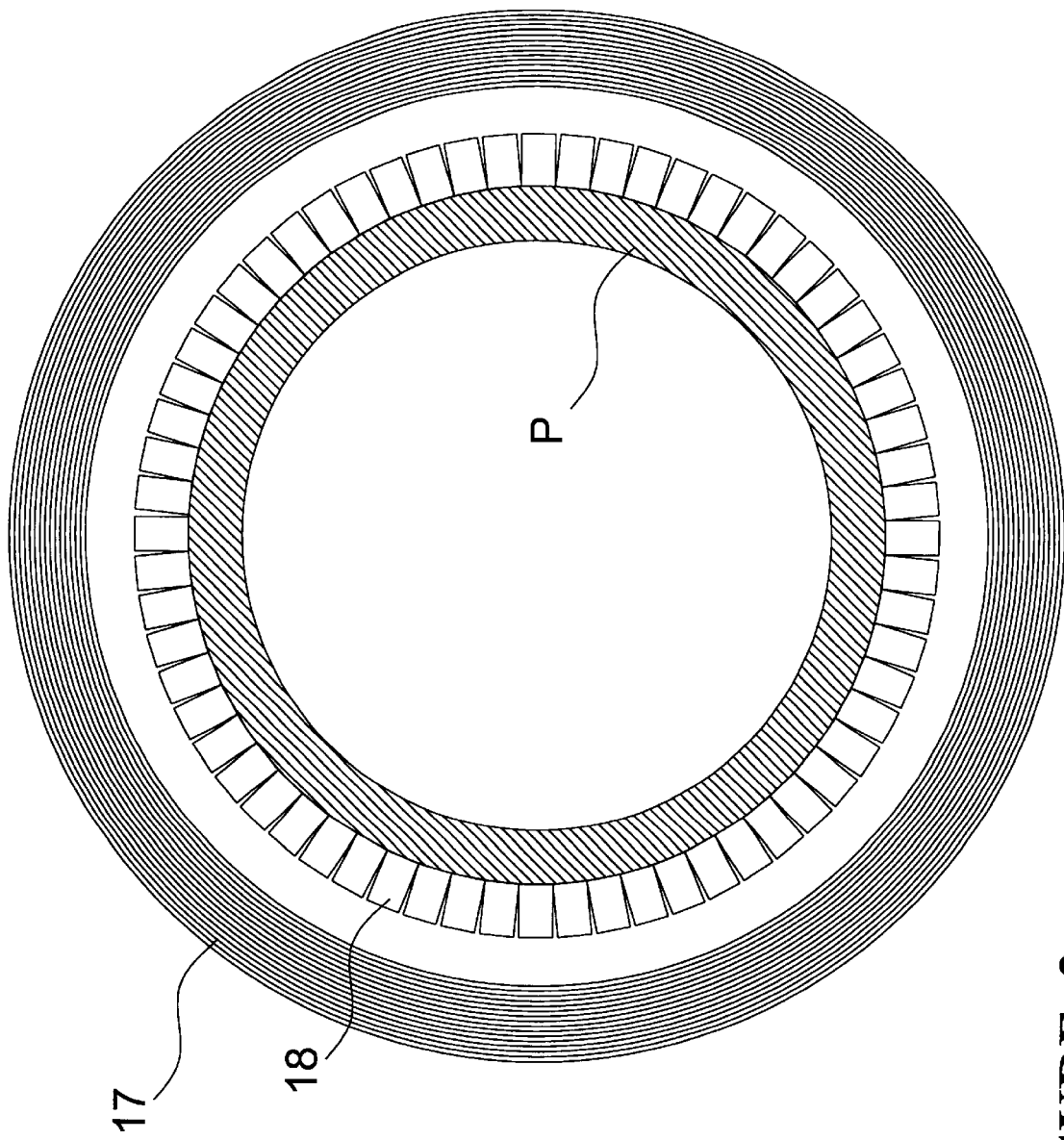
FIG. 2 illustrates the physical orientation of the sensors and DC magnetizing coil in relation to the tested ferrous tube.

Referring to FIG. 2, a cross-section of ferrous tube P to be tested is shown with the orientation of the linear Hall transducers 18 located around the immediate circumference of ferrous tube P. The magnetizing coil 3 windings 17 are shown oriented around the circumference of ferrous tube P.

Figure 3:
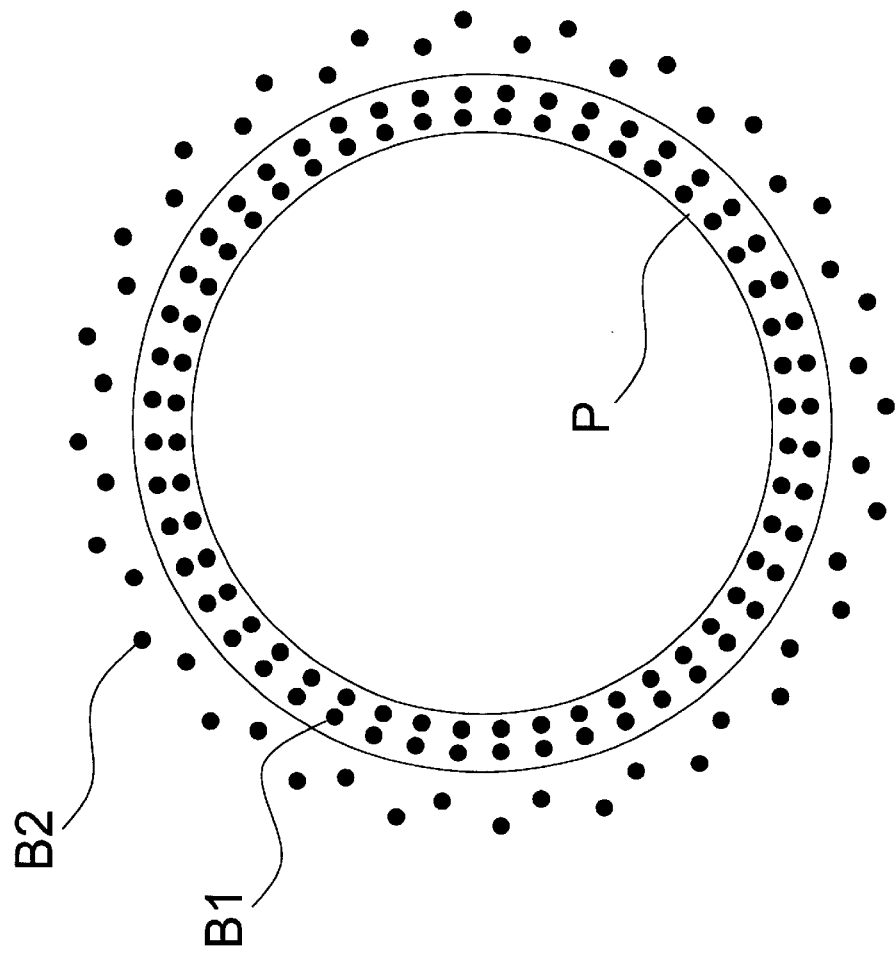
FIG. 3 is a diagram illustrating typical magnetic field lines in the body wall of and around the circumference of the ferrous tubing when no axially extending wall thickness defects are in the tested ferrous tube.

Referring to FIG. 3, ferrous tube P is shown with typical saturating magnetic field lines B1 linked to the body wall and driven by magnetizing coil 3. Magnetic field lines B2 are the free air magnetic field lines that never link with the ferrous tube P.

Figure 4:
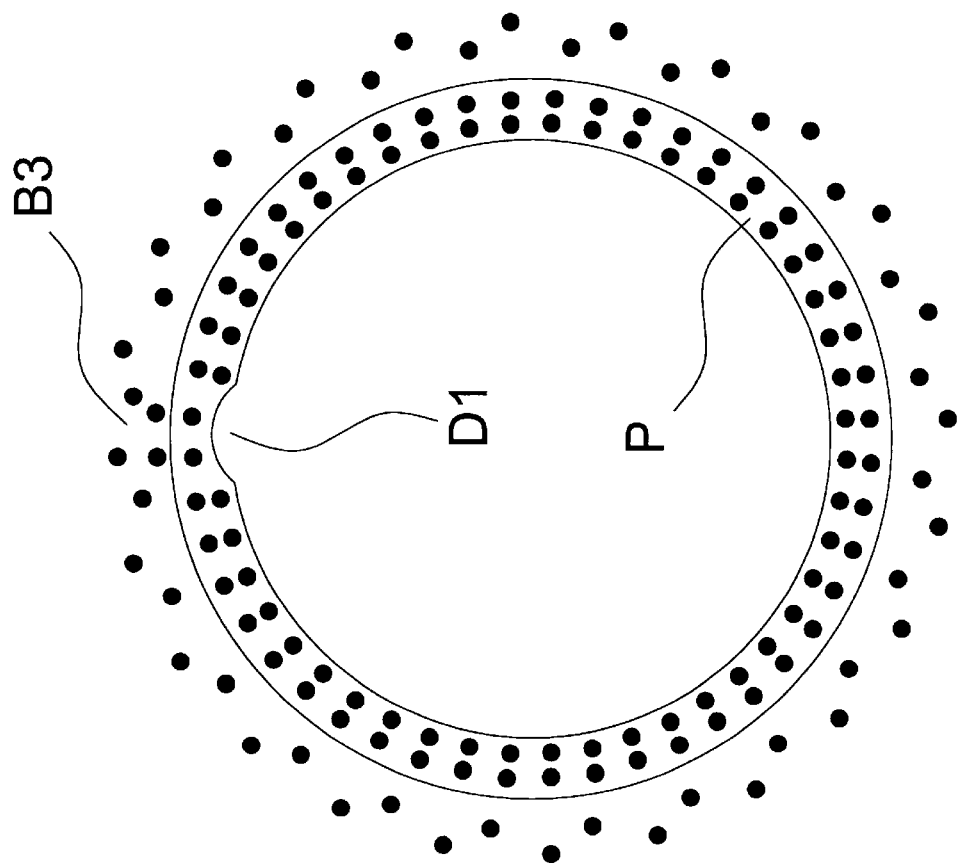
FIG. 4 is a diagram illustrating typical magnetic field lines around the circumference of the ferrous tube when an axially extending wall thickness defect exists in the tested ferrous tube.

Referring to FIG. 4, axially extending defect D1 is shown on the inner wall surface of ferrous tube P. Magnetic field lines B3 are shown to demonstrate how axially extending defect D1 leaks the magnetic field lines to the outer circumference of ferrous tube P. The magnetic field lines B3 are non-linking parallel flux.

Figure 5A:
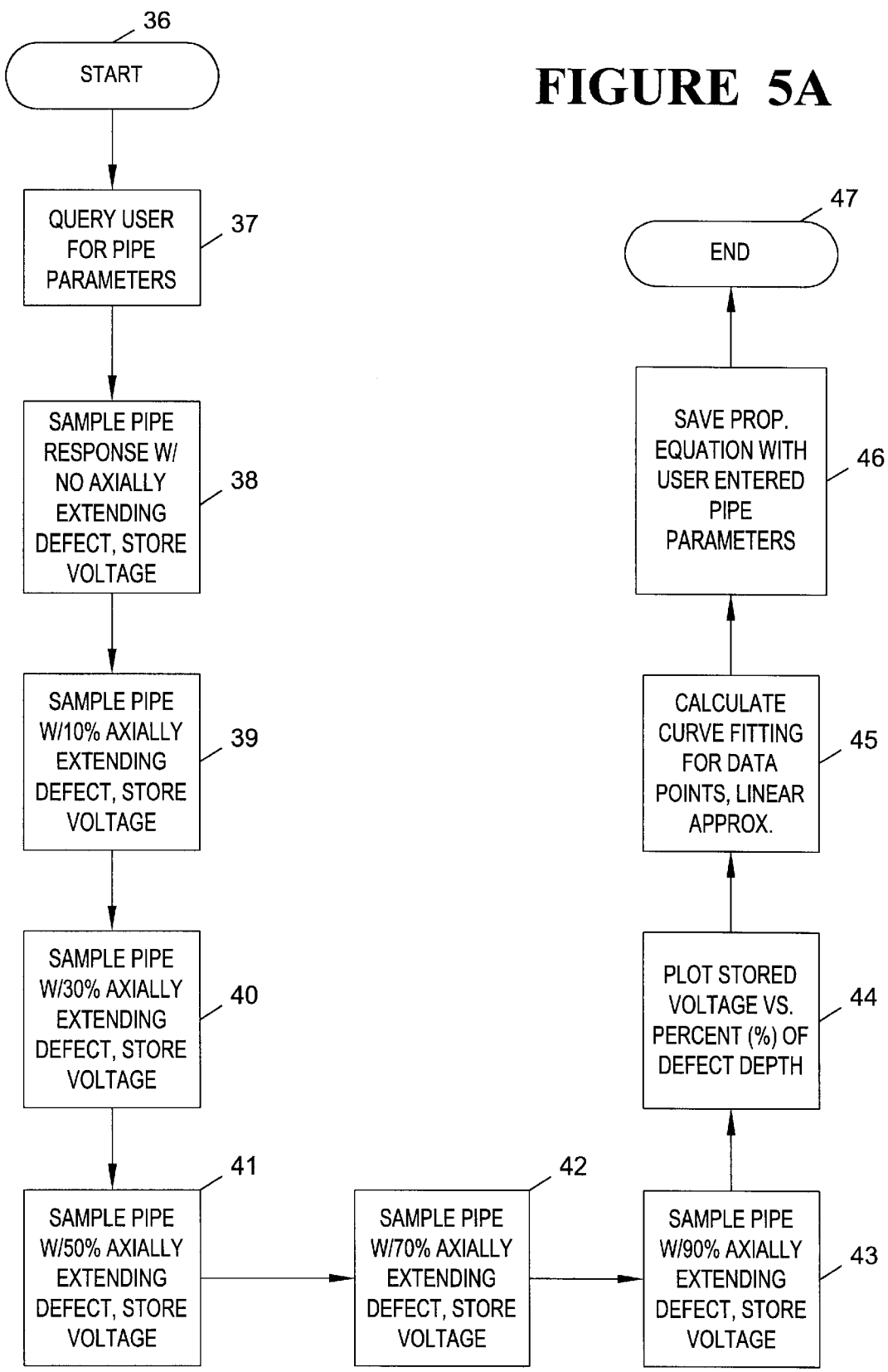
FIG. 5A is a flow chart illustrating the logical flow of the steps necessary to calculate the proportionality equations that are used to relate the measured parallel non-linking flux leakage to the percentage of wall loss in an axially extending defect.

Referring to FIG. 5A, processor 12 executes a program that follows the logical steps shown in this figure. Steps that are known to one of ordinary skill in the art that allow for typical computer functions such as saving, printing and user interaction are not shown or described because these steps are considered to be common and are easily obtainable with modern programming languages.

Step 36 starts the computer processing when processor 12 executes the proportionality equation calculation routine. Step 37 asks the end user for the parameters of the ferrous tube P such as weight, grade and wall thickness. Steps 38–43 utilize actual samples of ferrous tube that have physical and metallurgical characteristics similar to the ferrous tube P to be tested. Man made axially extending defects are created in the ferrous tube samples which mimic axially extending defects found in ferrous tube P to be tested. In this preferred embodiment, the depth of the man made axially extending defects are to be between ten and ninety percent of the nominal wall thickness of the ferrous tube samples, in twenty percent increments. However, it should be known that other defect depth percentages may be created and the man made defects may differ by increments other than twenty percent.

Step 38 obtains a typical voltage response from the ferrous tube sample when no axially extending defects exist. Processor 12 conducts for a predetermined period (one second in this preferred embodiment) an analog to digital conversion of voltage responses coming from the linear Hall transducers mounted in inspection shoes 2. Processor 12 retrieves the analog to digital converted voltage responses from its random access memory and averages the voltage responses to obtain a typical voltage response, which is stored for later use.

Step 39 obtains the voltage response of an axially extending defect that is equal to ten percent of the nominal wall thickness of the ferrous tube sample. Step 40 obtains the voltage response of an axially extending defect that is equal to thirty percent of the nominal wall thickness of the ferrous tube sample. Step 41 obtains the voltage response of an axially extending defect that is equal to fifty percent of the nominal wall thickness of the ferrous tube sample. Step 42 obtains the voltage response of an axially extending defect that is equal to seventy percent of the nominal wall thickness of the ferrous tube sample. Step 43 obtains the voltage response of an axially extending defect that is equal to ninety percent of the nominal wall thickness of the ferrous tube sample.

Step 44 plots each stored voltage response from the man made axially extending defects versus the equivalent percentage of the depth of the man made defect in the ferrous tube samples. Step 45 calculates a proportionality equation, which is an equation that best represents a curve substantially defined by the plotted voltage responses from each of the man made axially extending defects, by applying a curve fitting technique to the plotted voltage responses. In this preferred embodiment, the curve fitting technique calculates the proportionality equation according to a linear fit equation (e.g., $\%(i) = \text{slope} * \text{Vresp}(i) + \text{intercept}$). The proportionality equation is necessary because different types of ferrous tube leak magnetic flux at different rates for similar types of defects. However, the rate of flux leakage must still be related to the depth of the axially extending defect through a proportionality equation to obtain accurate percentage measurements.

Although the preferred curve fitting technique calculates the proportionality equation according to a linear fit equation, ferrous tubes do not always leak magnetic flux in a linear fashion with respect to the depth of the axially extending defects. Consequently, other equations that best represent a curve substantially defined by the plotted voltage responses from each of the man made axially extending defects may be calculated. Examples of such equations include a non-linear fit equation (e.g., $\% = f(\text{Vresp}, a)$, where a is the set of coefficients) and an exponential fit equation (e.g., $\%(i) = a * e^{d*\text{Vresp}(i)}$). Step 46 stores the proportionality equation with the user entered pipe parameters in a database for later retrieval. Step 47 ends the proportionality equation routine.

Figure 5B:
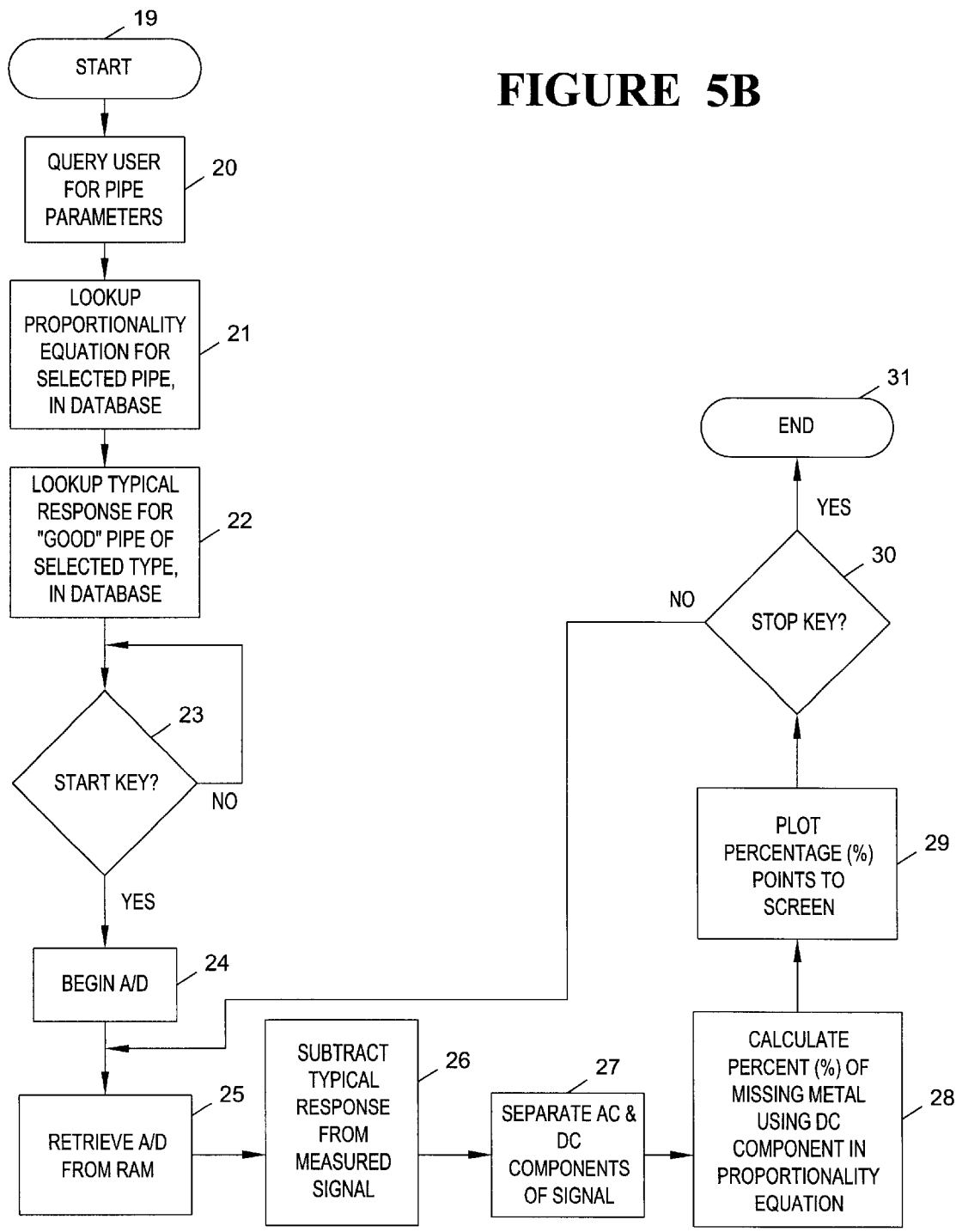
FIG. 5B is a flow chart illustrating the logical flow of the digital signal processing steps employed in the ferrous tube tester.

Referring to FIG. 5B, processor 12 executes a program that follows the logical steps shown in this figure. Steps that are known to one of ordinary skill in the art that allow for typical computer functions such as saving, printing and user interaction are not shown or described because these steps are considered to be common and are easily obtainable with modern programming languages. Step 19 starts the computer processing when processor 12 executes the main signal processing routine.

Step 20 asks the end user for the parameters of the ferrous tube P such as weight, grade and wall thickness. Step 21 uses the values entered in step 20 to look up the proportionality equation for the selected tube type in a database that has been created from the proportionality equation routine described in steps 36–47. Step 22 looks up the typical voltage response for the selected tube type as previously determined in step 38 of the proportionality equation routine. This typical voltage response is a baseline to which other tubes of similar type can be compared.

Figure 8:
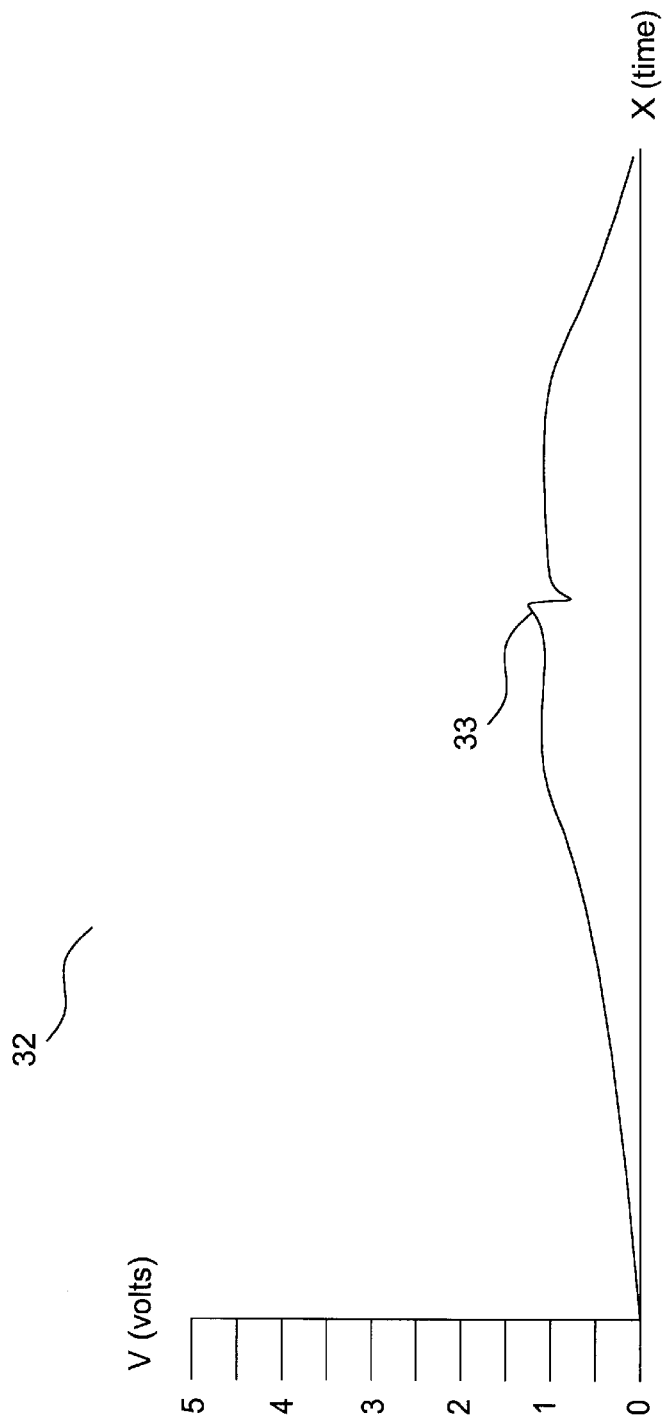
FIG. 8 is a typical computer generated chart output illustrating an unconditioned signal from the tested ferrous tube before the signal has been processed by the digital signal processing algorithms.

Step 23 waits for the end user to press the start key on keyboard 15. If no start key has been pressed, processor 12 continues to execute step 23 repeatedly. If a start key has been pressed, processor 12 continues to step 24 which begins an analog to digital conversion of voltage responses coming from the linear Hall transducers mounted in inspection shoes 2. In step 25, processor 12 retrieves the analog to digital converted voltage responses from its random access memory. An example of the retrieved raw signal is shown in FIG. 8, before any digital signal processing has been performed.

In step 26, the typical voltage response for the selected tube type, which was looked up in the database in step 22, is subtracted from each of the newly measured and digitized voltage responses obtained from the linear Hall transducers to develop difference voltage responses. Any difference between the typical response for the selected tube type and the measured voltage responses indicates that some form of defect exists within the ferrous tube body wall.

In step 27, alternating AC voltages are separated from the relatively constant DC voltages of the difference voltage responses for the ferrous tube P to develop DC voltage response components. The DC voltage response components are developed utilizing digital signal processing techniques well known to one of ordinary skill in the art. However, it should be understood that similar results could be obtained using analog electronics, but would prove to be much more complex in duplicating the digital algorithms. Additionally, some extremely low AC frequencies are considered as DC for all practical purposes in applications such as this. Therefore, it should be understood that the AC/DC separation algorithms in step 27 can be tuned to allow such low frequency signals to come through and be processed by the remaining digital signal processing algorithms.

Figure 9:
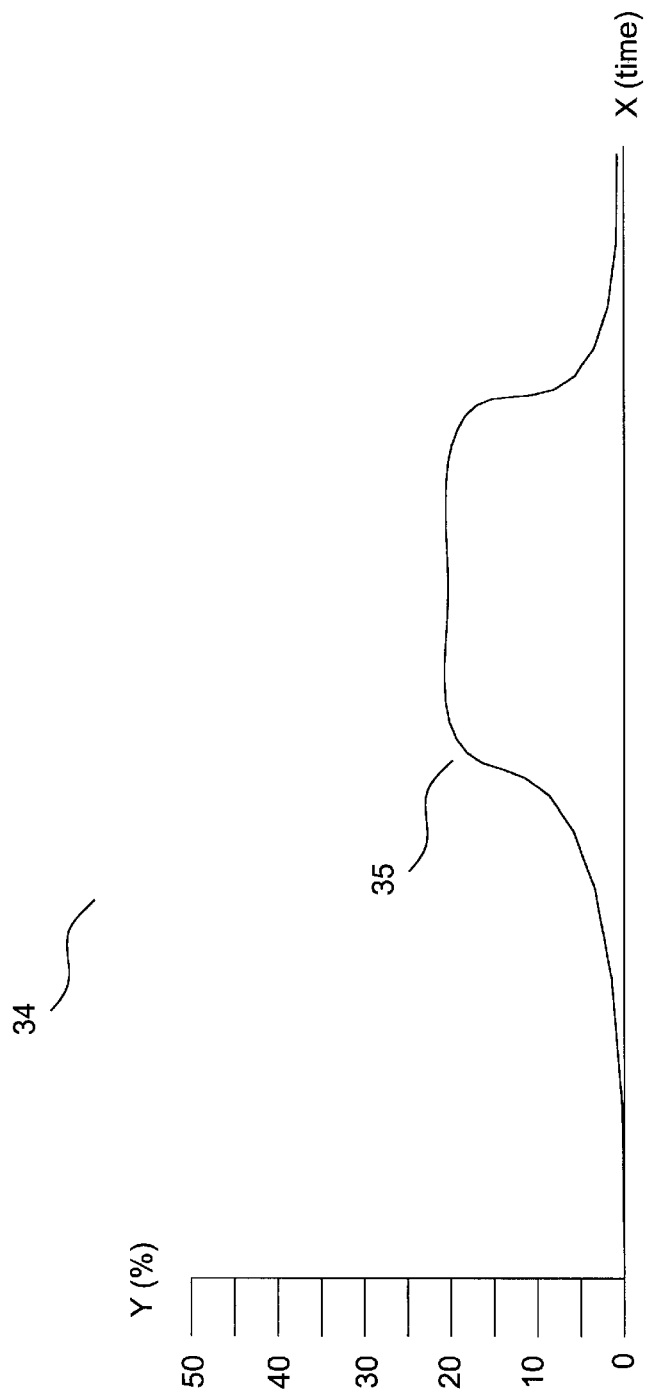
FIG. 9 is a typical computer generated chart output illustrating a conditioned signal from the tested ferrous tube after the signal has been processed by the digital signal processing algorithms.

In step 28, the actual percentage of material missing from the body wall of ferrous tube P is calculated by utilizing the proportionality equation obtained in step 21. Each DC voltage response component, which results after the AC/DC separation from step 27, is substituted into the proportionality equation to render the actual percentage of material missing from the body wall of ferrous tube P. Processor 12 plots the digital percentage values on a graph displayed on screen 11 so that the end user may be informed of the condition of ferrous tube P. An example of the resulting computer generated graph is shown in FIG. 9. In step 30, processor 12 checks if the end user presses the stop key. If the stop key is not pressed, processor 12 returns to step 25 to repeat the digital signal processing loop over again with the next group of values obtained from the linear Hall transducers. If the stop key is pressed, processor 12 ends the testing process by executing step 31.

Figure 6:
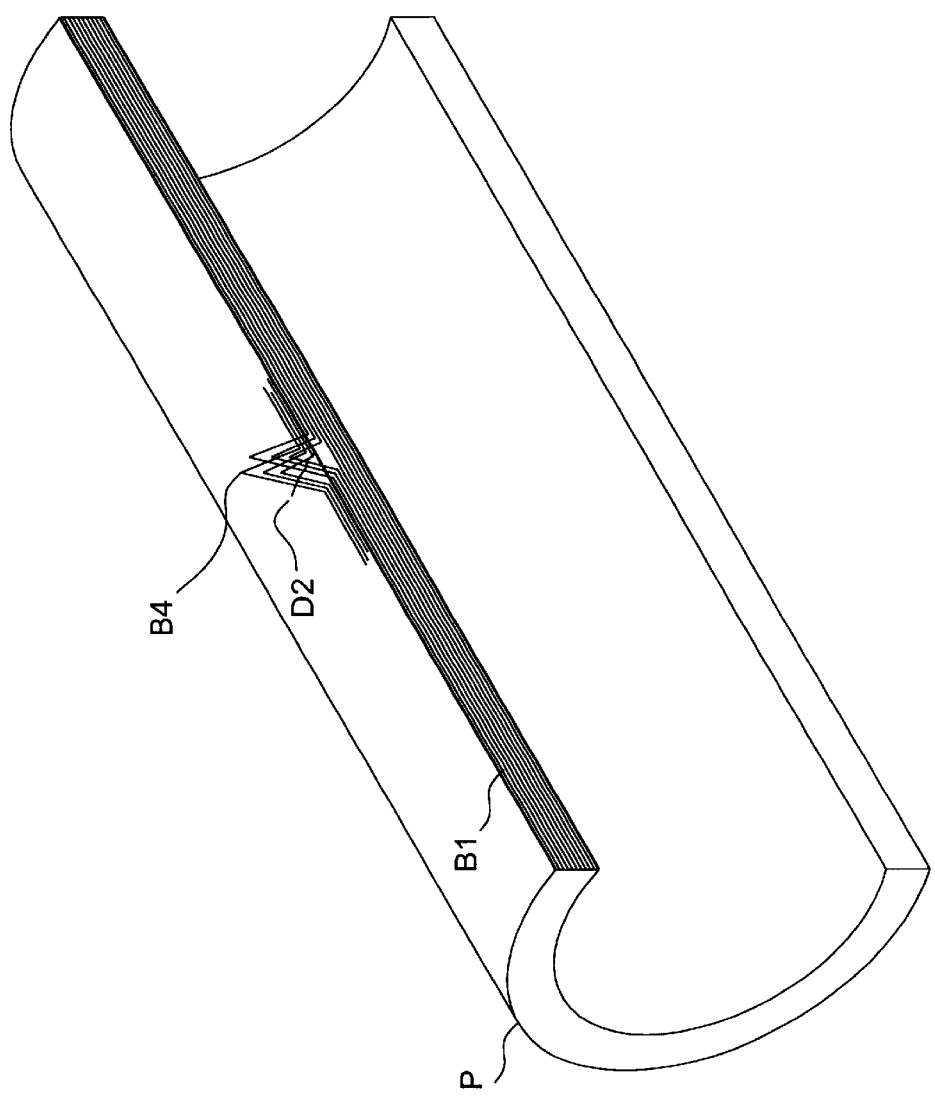
FIG. 6 is a diagram illustrating perpendicular flux leakage at the site of a transversely oriented, localized defect in the tested ferrous tube.

Referring to FIG. 6, ferrous tube P is shown with saturating magnetic field lines B1 within the body wall of the tested ferrous tube being tested. Defect D2 is representative of a transversely oriented defect such as a crack or pit, which generates perpendicular magnetic flux leakage lines B4.

Figure 7:
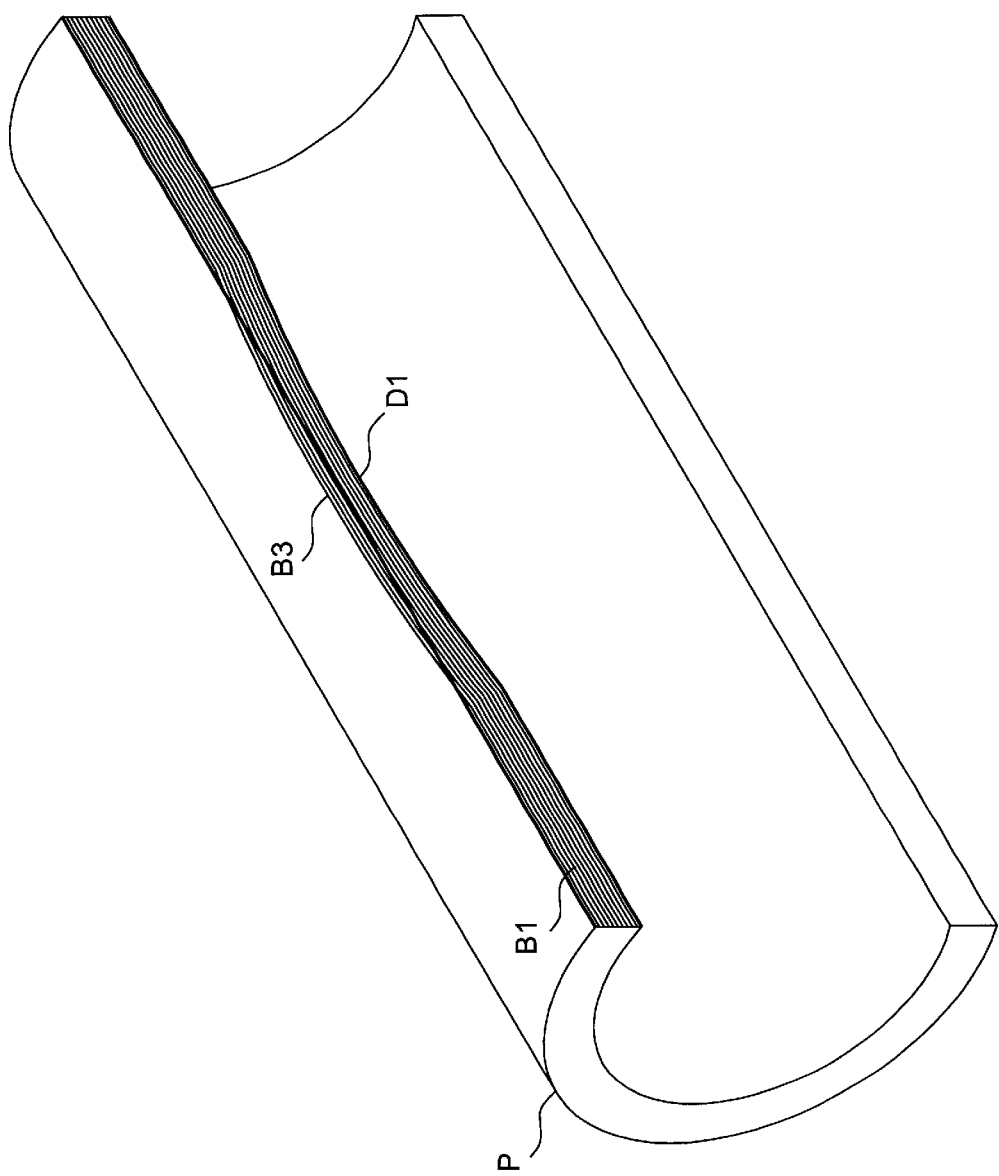
FIG. 7 is a diagram illustrating parallel non-linking flux leakage at the site of an axially extending wall thickness defect in the tested ferrous tube.

Referring to FIG. 7, ferrous tube P is shown with saturating magnetic field lines B1 within the body wall of the tested ferrous tubing. Axially extending defect D1 is shown which is creating non-linking parallel flux leakage at the immediate circumference of the ferrous tubing being tested. When FIG. 7 is compared to FIG. 6, it is easy to see why axially extending defects have previously been undetected by existing ferrous tube testers. The flux leakage, which is the result of axially extending defect DI, is of such a gradual nature that existing systems either stripped this valuable information out with DC blocking capacitors or the low level of signal from the non-linking parallel flux leakage was never detected because typical ferrous tube testers have been configured to monitor for perpendicular flux leakage as shown in FIG. 6. Perpendicular flux leakage renders such a large voltage when compared to the non-linking parallel flux leakage that axially extending defect information is overwhelmed by localized and transverse defects. This is why the AC and DC components of the signal must be separated. The localized and transverse defects create AC signals. These AC signals must be removed so the remaining DC signal component may be evaluated against the values from a typical good tube of the same type being tested.

FIG. 8 is a graph 32 which is representative of the raw voltage being returned from the linear Hall transducers before digital signal processing has been performed. The X-axis is representative of time as ferrous tube tester 1 passes along the ferrous tube P, or ferrous tube P is passed through ferrous tube tester 1. Item 33 is the AC signal component resulting from a localized or transverse defect similar to defect D2 shown in FIG. 6. The Y-axis of chart 32 represents volts as produced by the linear Hall transducers.

FIG. 9 is a graph 34 which shows the percentage of body wall missing from ferrous tube P at the site of axially extending defect D1. The X-axis is representative of time as ferrous tube tester 1 passes along the ferrous tube, or ferrous tube P is passed through ferrous tube tester 1. The Y-axis is representative of percentage of missing material in the body wall of ferrous tube P. Item 35 is the plot of the calculated percentage values using the proportionality equation obtained in step 21 after the typical response of the tube type being tested is subtracted from the measured values from the linear Hall transducers and the AC component is removed from the remaining signal as provided for in step 27.

Although the present invention has been described in terms of the foregoing embodiment, such description has been for exemplary purposes only and, as will be apparent to those of ordinary skill in the art, any alternatives, equivalence, and variations of varying degree will fall within the scope of the present invention. That scope accordingly, is not to be limited in any respect by the foregoing description, rather, it is defined only by the claims that follow.

I claim:

1. A method for detecting and measuring axially extending defects in ferrous tube, comprising the steps of:

developing a typical voltage response from a ferrous tube having known characteristics;

developing a proportionality equation from the ferrous tube having known characteristics;

inducing a magnetic field in a tested ferrous tube;

measuring voltage responses from the tested ferrous tube;

subtracting the typical voltage response from each of the measured voltage responses to develop difference voltage responses;

digital signal processing each difference voltage response to develop DC voltage response components;

substituting each DC voltage response component into the proportionality equation; and displaying the results from the substitution of each DC voltage response component into the proportionality equation to illustrate axially extending defects in the tested ferrous tube.

2. The method according to claim 1, wherein substituting each DC voltage response component into the proportionality equation renders a percentage of material missing for each axially extending defect in the ferrous tube.

3. The method according to claim 2, wherein displaying the results from the substitution of each DC voltage response component into the proportionality equation illustrates the percentage of material missing for each axially extending defect in the ferrous tube.

4. The method according to claim 1, wherein the step of developing a typical voltage response from a ferrous tube having known characteristics comprises the steps of:

inducing a magnetic field in a ferrous tube having known characteristics;

measuring for a predetermined period voltage responses from the ferrous tube having known characteristics; and averaging the voltage responses to develop the typical voltage response.

5. The method according to claim 1, wherein the step of developing a proportionality equation from a ferrous tube having known characteristics comprises the steps of:

inducing a magnetic field in a ferrous tube having known characteristics;

measuring a voltage response from at least two known axially extending defects in the ferrous tube having known characteristics;

plotting the voltage responses from the at least two known axially extending defects in the ferrous tube having known characteristics; and applying a curve fitting technique to the plotted voltage responses from the at least two known axially extending defects to calculate the proportionality equation.

6. The method according to claim 5, wherein the proportionality equation represents a curve substantially defined by the plotted voltage responses from the at least two known axially extending defects.

7. The method according to claim 5, wherein the curve fitting technique calculates the proportionality equation according to a linear fit equation.

8. The method according to claim 5, wherein the curve fitting technique calculates the proportionality equation according to a non-linear fit equation.

9. The method according to claim 5, wherein the curve fitting technique calculates the proportionality equation according to an exponential fit equation.

10. The method according to claim 1, wherein the step of digital signal processing each difference voltage response to develop DC voltage response components separates alternating AC voltages from relatively constant DC voltages.

11. A method of developing a proportionality equation from a ferrous tube having known characteristics, comprising the steps of:

inducing a magnetic field in a ferrous tube having known characteristics;

measuring a voltage response from at least two known axially extending defects in the ferrous tube having known characteristics;

plotting the voltage responses from the at least two known axially extending defects in the ferrous tube having known characteristics; and applying a curve fitting technique to the plotted voltage responses from the at least two known axially extending defects to calculate the proportionality equation.

12. The method according to claim 11, wherein the proportionality equation represents a curve substantially defined by the plotted voltage responses from the at least two known axially extending defects.

13. The method according to claim 11, wherein the curve fitting technique calculates the proportionality equation according to a linear fit equation.

14. The method according to claim 11, wherein the curve fitting technique calculates the proportionality equation according to a non-linear fit equation.

15. The method according to claim 11, wherein the curve fitting technique calculates the proportionality equation according to an exponential fit equation.

16. An apparatus for detecting and measuring axially extending defects in ferrous tube, comprising:

an inspection head for inducing a magnetic field in a ferrous tube and for measuring voltage responses therefrom;

a processor for subtracting a typical voltage response from each of the measured voltage responses to develop difference voltage responses, for digital signal processing each difference voltage response to develop DC voltage response components, and for substituting each DC voltage response component into a proportionality equation; and a display that displays the result from the substitution of each DC voltage response component into the proportionality equation to illustrate axially extending defects in the tested ferrous tube.

17. The apparatus according to claim 16 wherein the processor further develops the typical voltage response from a ferrous tube having known characteristics and the proportionality equation from the ferrous tube having known characteristics.

18. The apparatus according to claim 16, further comprising an analog to digital converter for converting the measured voltage responses to processor readable signals.

19. The apparatus according to claim 16, further comprising a digital to analog signal converter for facilitating processor control over the inspection head.

20. The apparatus according to claim 16, wherein the inspection head comprises:

a magnetizing coil for inducing the magnetic field in the ferrous tube; and inspection shoes for measuring voltage responses from the ferrous tube.

21. The apparatus according to claim 20, further comprising a magnetizing coil power supply controlled by the processor to deliver power to the magnetizing coil.

22. The apparatus according to claim 20, further comprising a shoe power supply controlled by the processor to deliver power to the inspection shoes.

23. The apparatus according to claim 16, further comprising a user input device for allowing user input to the processor.

24. The apparatus according to claim 16, further comprising a memory associated with the processor for storing data and control software utilized by the processor.

25. The apparatus according to claim 16, farther comprising a printer that prints the from the substitution of each DC voltage response component into the proportionality equation to illustrate axially extending defects in the tested ferrous tube.

26. The apparatus according to claim 16, further comprising a removable storage media for storing the results from the substitution of each DC voltage response component into the proportionality equation.

* * * * *